(12) United States Patent
Gibbs

(10) Patent No.: US 6,905,486 B2
(45) Date of Patent: *Jun. 14, 2005

(54) DEVICE FOR TARGETED, CATHETERIZED DELIVERY OF MEDICATIONS

(76) Inventor: David Gibbs, 13 Richmond Rd., Ottawa, Ontario (CA), K1Y 2X1

( * ) Notice: Subject to any disclaimer, the term of this patent is extended or adjusted under 35 U.S.C. 154(b) by 0 days.

This patent is subject to a terminal disclaimer.

(21) Appl. No.: 10/234,767

(22) Filed: Sep. 5, 2002

(65) Prior Publication Data
US 2003/0032939 A1 Feb. 13, 2003

Related U.S. Application Data

(63) Continuation-in-part of application No. 09/420,004, filed on Oct. 18, 1999, now Pat. No. 6,468,248, which is a continuation of application No. 09/255,442, filed on Feb. 22, 1999, now abandoned, which is a continuation of application No. 09/022,314, filed on Feb. 11, 1998, now abandoned, which is a continuation of application No. 08/471,372, filed on Jun. 6, 1995, now Pat. No. 5,762,639.

(51) Int. Cl.$^7$ ................................................ A61M 5/00
(52) U.S. Cl. ........................ 604/264; 604/272; 433/80; 433/165; 606/80
(58) Field of Search .............................. 604/510, 240, 604/272, 264, 164.01–164.08; 600/567, 80; 606/180, 96; 433/80, 165

(56) References Cited

U.S. PATENT DOCUMENTS

| | | | |
|---|---|---|---|
| 4,142,517 A | * | 3/1979 | Contreras Guerrero de Stavropoulos et al. . 600/567 |
| 5,133,359 A | * | 7/1992 | Kedem ........................ 600/567 |
| 5,378,149 A | * | 1/1995 | Stropko ........................ 433/80 |

* cited by examiner

Primary Examiner—Kevin C. Sirmons
(74) Attorney, Agent, or Firm—Neil Teitelbaum; Teitelbaum & MacLean

(57) ABSTRACT

Apparatus and method for catheterized delivery or infusion of medication and anaesthesia are disclosed. The perforating catheter is first used to perforate the periodontal ligament and/or the cortical plate of bone tissue, and is then left in place and used as a catheter for insertion of a hypodermic needle of smaller gauge to deliver medication or anaesthesia to a target area. The perforator is a bevelled needle for drilling into the ligament or bone tissue. For drilling, the device comprises an adaptor which transmits the rotational movement from a dental hand piece or the like to the bevelled needle. A cap is also included for protecting the bevelled needle during storage of the device. The adaptor may have a rod which extends axially into the bevelled needle when the device is assembled for drilling. The rod is used to prevent the debris resulting from drilling from blocking the passage in the bevelled needle. As well, the rod reinforces the needle and maintains the alignment between the perforator and the adaptor for improved drilling efficiency. An adapter is disclosed which couples with the catheter once in place easing access to supply medication to difficult to reach areas.

6 Claims, 7 Drawing Sheets

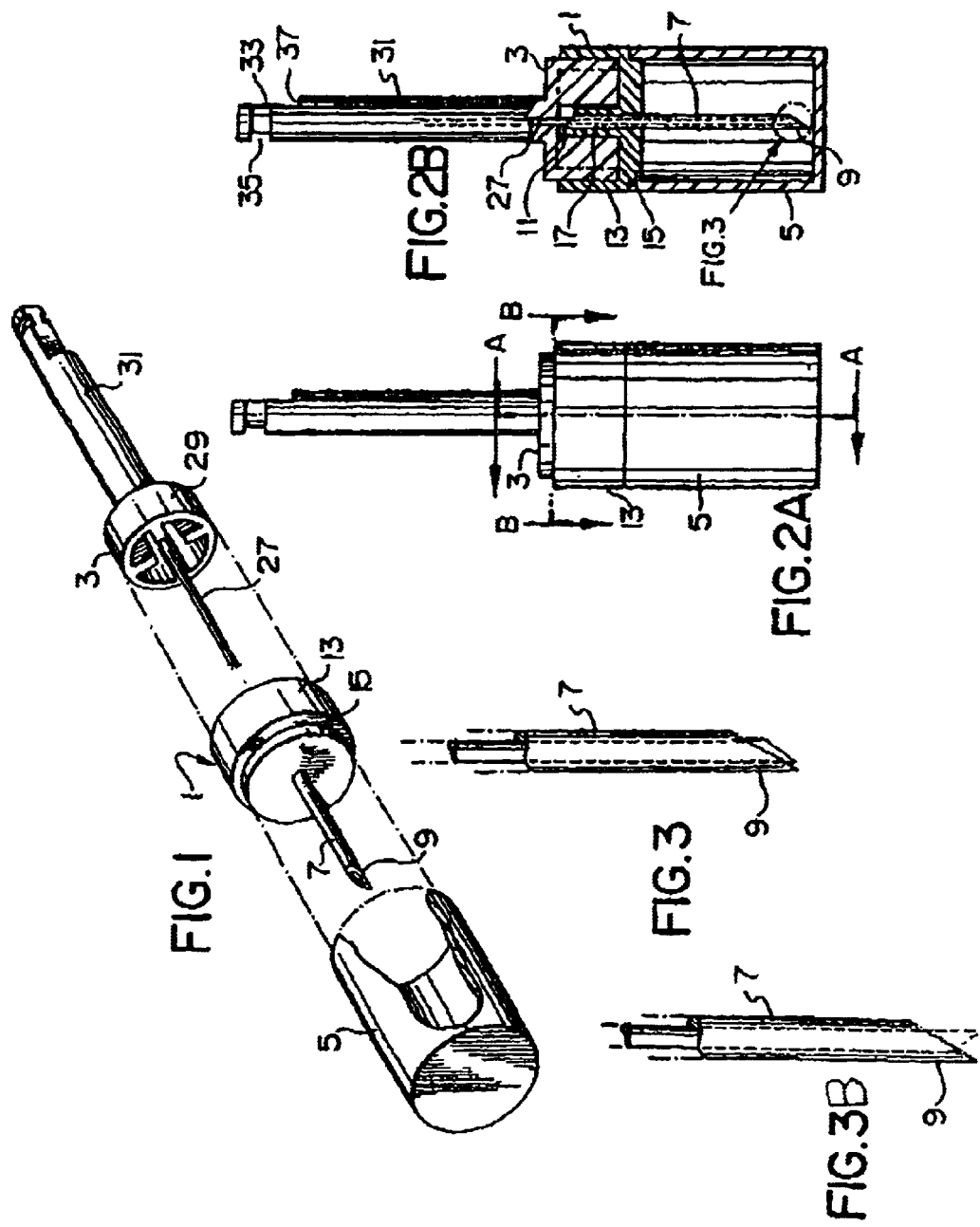

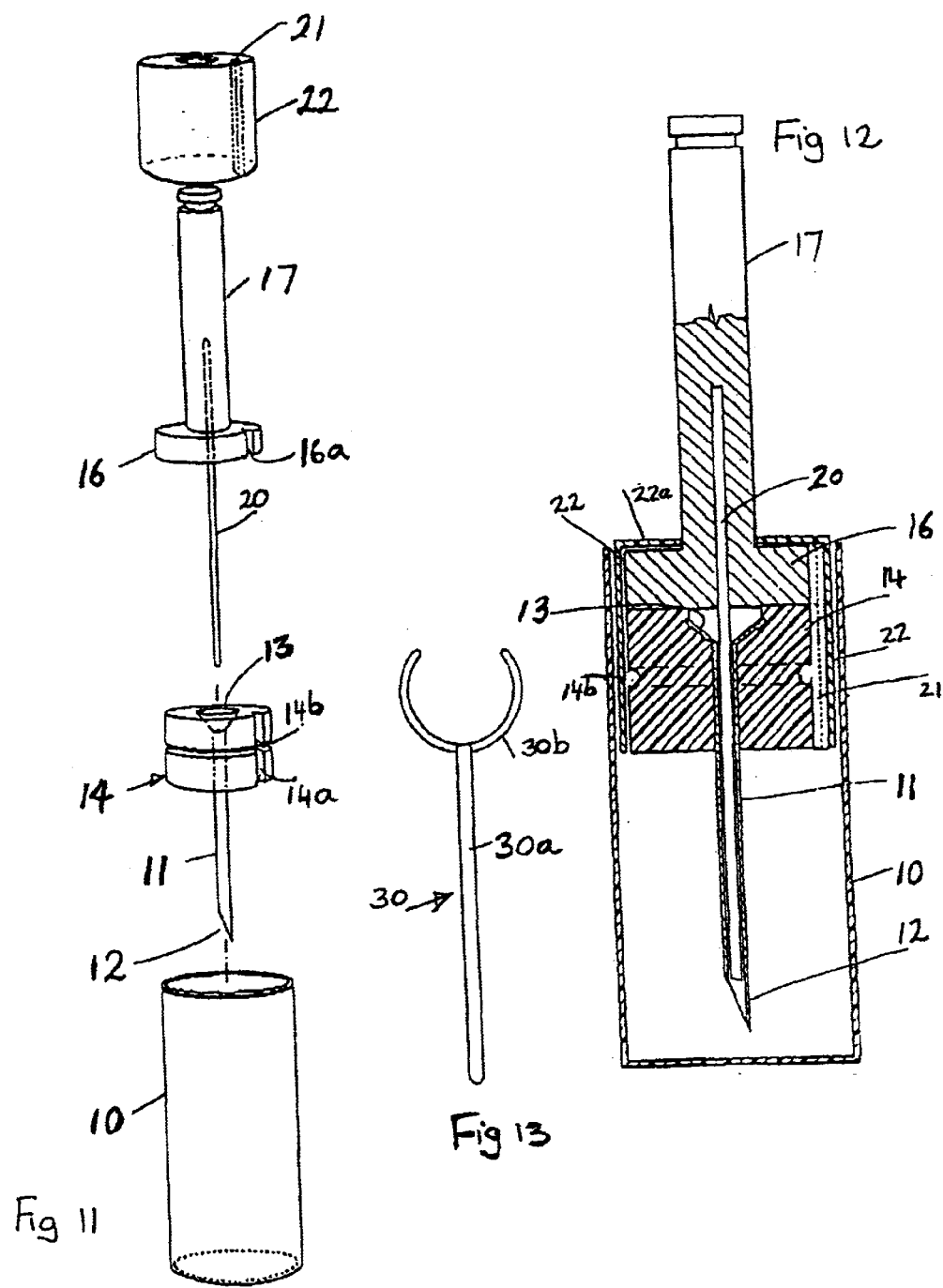

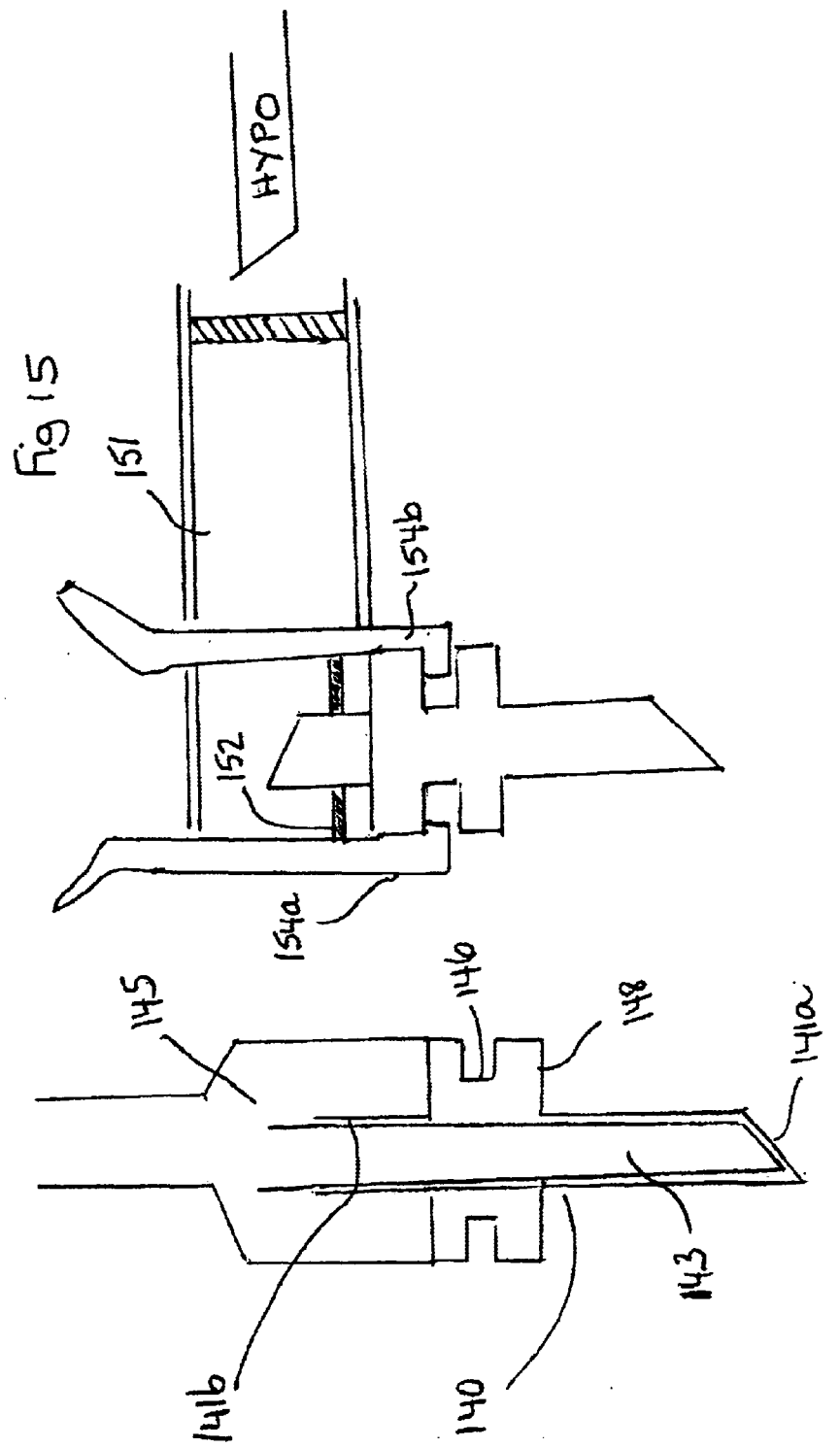

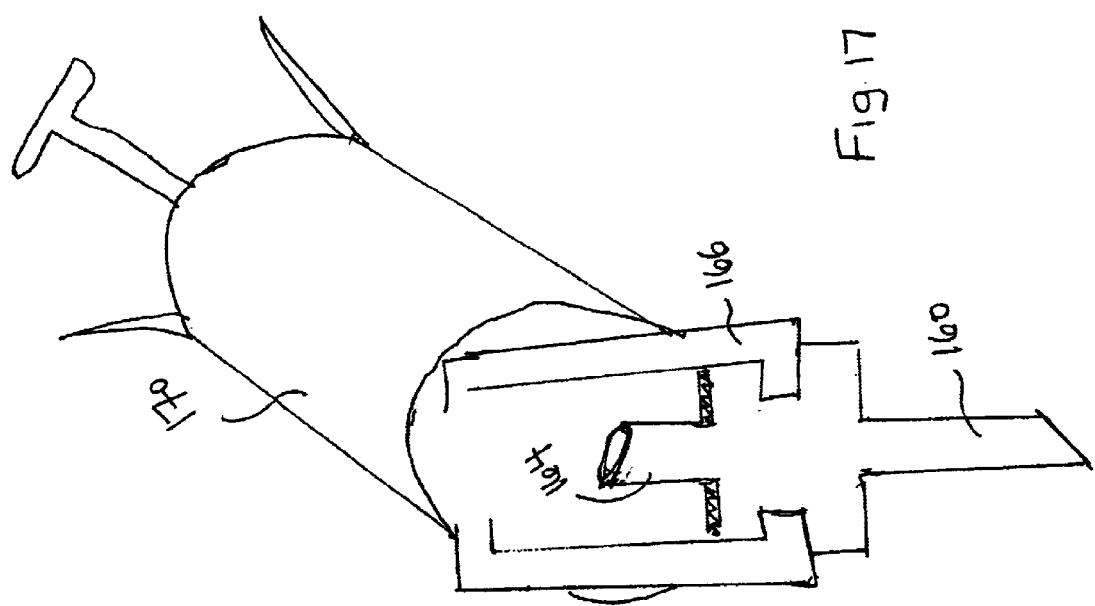

DEVICE FOR TARGETED, CATHETERIZED DELIVERY OF MEDICATIONS

This invention is a continuation-in-part parent application to Ser. No. 09/420,004 filed Oct. 18, 1999 now U.S. Pat. No. 6,468,248, which is a continuation of patent application to Ser. No. 09/255,442 filed Feb. 22, 1999 now abandoned, which is a continuation of patent application Ser. No. 09/022,314 filed Feb. 11, 1998 now abandoned, which is a continuation of patent application Ser. No. 08/471,372, filed Jun. 6, 1995 now issued as U.S. Pat. No. 5,762,639.

FIELD OF THE INVENTION

The present invention provides for a simple method and device for infusing or injecting medication; it is applicable to medical or dental and the like procedures. More particularly, the invention is directed to catheterized delivery of anesthesia and other medication. More particularly still, it is directed to catheterized delivery of dental anaesthetic to a targeted nerve and to an apparatus for such delivery.

BACKGROUND OF THE INVENTION

There are a variety of methods currently in use for providing local anaesthetic in dentistry. These methods and apparatuses however all have disadvantages, either being difficult for practitioners to perform or painful and unpleasant to the patient.

An example of a method used currently in dentistry is the infiltration method, whereby a local anaesthetic solution is injected into the soft tissue of gingiva. In doing so, the solution eventually passes through the cortical plate affecting the nerve bundle entering the tooth. Disadvantages of this method include the delay of onset of anaesthesia after the injection and, in most cases, ballooning of the injected tissue. As well, there is an extended period of time for recovery of the tissue until return to normal condition.

Another method which is currently used is the regional block method whereby an anaesthetic solution is injected locally in proximity to the nerve trunk as it enters the bone. Disadvantages of this procedure are that it is extremely difficult to locate the nerve trunk, there is discomfort to the patient and a delay for the anaesthetic to take effect. As in the case of the infiltration method, this method necessitates a long recovery period for tissue to return to normal.

At present, two types of apparatus have been used to perform intra-osseous anaesthesia. These are surgical burs used to perforate the cortical plate and the villet injectors.

The use of a surgical bur has disadvantages in that burs are expensive and they have to be sterilized between uses or a new bur used each time. In addition, the method is slow, requiring the attached gingiva and periosteum to be anaesthetized before the cortical plate is perforated. The villet injector is an apparatus that serves both as a perforator and injector. It uses specially designed needles rotated by a conventional dental motor. A disadvantage of this device is that the needle often becomes clogged with pulverized bone which obstructs the passage in the needle and prevents injection of the anaesthetic solution. It is generally difficult to remove the clogging material from the needle and often the use of a second needle is necessary. Other disadvantages of this method include the initial capital cost of the instrument purchase, and the cost of the needles which are somewhat expensive. In addition, the design of the instrument makes access to various parts of the mouth difficult and sometimes impossible.

Intra-osseous and targeted root-canal nerve anaesthesia have not become popular for the reason that there has not been a practical technique of making the injections successfully. For example, there has been a general belief that this method is radical and to be restored to only if nerve block and infiltration anaesthetic do not accomplish the desired result. However, intra-osseous and targeted injections produce positive, more profound anaesthesia and could be made with less pain than either of the other types according to the present invention.

Targeted anaesthesia has several advantages over prior art nerve block or infiltration methods. There is no feeling of numbness in the tongue, cheek, or lips during or after the injection and there is no after-pain. The anaesthetic is profound and acts immediately alleviating the necessity of waiting for the anaesthetic to take effect as with the nerve block and infiltration methods. Furthermore, as only a few drop, of anaesthetic are injected, there is no feeling of faintness or increasing of the pulse rate.

To achieve targeted anaesthesia one must gain access, it intra-osseous, to the cancellous bone by going through the cortical layer; or to the bottom of the tooth, if root-canal targeted anaesthesia is desired. Because of instant anaesthesia and profound pulpal anaesthesia, there is a much greater control over the region one wishes to anaesthetize, resulting in a much smaller dose of anaesthetic; as well as, of course, other medication, where applicable.

U.S. Pat. No. 5,173,050 (Dillon) discloses a dental apparatus for perforating the cortical plate of human maxillary and mandibular bones. The apparatus of Dillon comprises a metal needle moulded into a plastic shank. The shank is being formed with means for cooperation with a dental hand piece for transmitting the rotational movement to the needle. The needle used for drilling is solid and has a sharp bevelled free end. The apparatus described by Dillon is disposable.

However, the device disclosed in Dillon's patent cannot be used as a catheter for injecting anaesthetic by inserting a hypodermic needle through the drilling needle. As well, the device disclosed by Dillon is not provided with means for blocking entry of bone debris into the needle passageway. In addition, the direct connection between the hand piece and the perforator does not provide for a safe and reliable barrier against bacteria passing from the needle to the hand piece.

U.S. Pat. No. 3,534,476 (Winters) discloses a drilling and filling root canal apparatus. The drilling is performed by a drill having a central bore. The depth of the root canal is determined in advance and a stop is placed on the drill to limit the depth of drilling. The device is provided with a flexible rod which is pushed into the root canal so that the drill is directed along this road to follow the contour of the canal so that resulting bore will have an uniform diameter which is free of shoulders or ledges. The apparatus disclosed by winters is concerned with enlarging the root canal after the nerve has been extracted. This apparatus is not used for injecting medication in close proximity to a targeted area for treatment or anaesthetic.

U.S. Pat. No. 4,944,677 (Alexandre) discloses a smooth hollow needle with a bevelled point for drilling a hole into the jawbone near the apex of the tooth to be anaesthetized. Thereafter, the drilling device 13 removed from the jaw, and a hypodermic needle of substantially the same gauge is inserted into the hole and anaesthesia is injected. Thus, there is no catheterized delivery of medication, with the attendant disadvantage that the pre-drilled hole may be difficult to locate when inserting the hypodermic needle.

One significantly older United States patent that is discussed by Alexandre (above) is U.S. Pat. No. 2,317,648 (Siqveland) granted in 1943. In addition to the disadvantage mentioned by Alexyandre, the fact that Siqveland teaches use of threaded sleeve which penetrates the bone during drilling and is left (screwed) in the bone to serve as a guide for insertion of the actual injection needle. Due to the cost of such a device, it cannot be made disposable; but more importantly, for the threaded sleeve to be securely fastened in the bone it would have to rotate at a much slower speed than the drill (as in Siqveland) or the drilling catheter (as in the present invention).

Several other U.S. patents such as U.S. Pat. No. 5,332,398 in the name of Miller, and U.S. Pat. No. 4,969,870 in the name of Kramer have followed the teaching of Siqveland wherein the catheter is at least somewhere along its outer periphery threaded, or designed to implant itself fixedly within the bone it is being disposed in; Furthermore, designs of this type require slowly turning the drilling shaft (or catheter sleeve) into the bone until resistance is encountered at which point the catheter is determined to be in place.

Over the past 50 year or so, and at least since the invention of Siqveland, patented in 1943, devices and processes for intraosseous anesthesia have been developed and refined. However, heretofore, no other inventors have provides a useful, workable convenient and inexpensive solution that affords all of the benefits provided by this invention. For example, non of the prior art devices allow a motorized handpiece to drive a small intraosseous catheter/drill having a rod/drill therein wherein the device can be placed by drilling at high or slower speeds and removed by simple withdrawal by pulling out the catheter. Most of the effort in this field had been directed toward longer term delivery of medication wherein the catheters have had some means of latching into the bone for more permanent placement. Furthermore, the instant invention does not suffer from may of the drawbacks of inserting the needle/drill into the bore being cut by the end tip of the drill, since the outside walls of the needle/drill are of a uniform diameter and non-varying. With the long-felt want of this device, in the past decade in view of the many publications in this field, no such optimal device has been suggested.

In contrast to the prior art, the instant invention provides a dual purpose perforator which includes a needle/sleeve that serves as a relatively high-speed drill bit and which serves as a catheter chat is removable by withdrawing it by pulling it out, and not by unscrewing it. The perforator has a substantially uniform outer diameter and has a smooth non-threaded outer surface; preferably, the catheter is a larger gauge needle than the removable rod contained within which may also be in the form of a beveled needle for preventing bone, skin and debris from entering the catheter during entry into the bone. A hypodermic needle of same gauge as the rod is later placed in the catheter after the rod is removed.

Advantageously, the beveled end of the rod assists the cutting of the opening into the bone along with the perforator as they are both rotated by the dental hand piece they are coupled therewith.

To our knowledge, there are no prior art patents, which teach the use of a perforator having a hypodermic needle-like cutting tool wherein the outer diameter is uniform allowing both precise cutting of a small hole, and allowing easy removal by simply pulling the device out without unthreading, wherein the perforator has an upper end adapted to be connected to a motorized dental hand piece; and, wherein the perforator has a rod therein which turns with the perforator needle-like cutting tool assisting in preventing debris from entering the perforator; and wherein the rod is itself a needle-like cutting tool assisting in the cutting of the opening.

To our knowledge, aside from the parent patent application, now issued as U.S. Pat. No. 5,332,398 and U.S. Pat. No. 5,779,708 in the name of Wu, issued Jul. 14, 1998 there are no prior art patents, which teach the use of a perforator having a hypodermic needle-like cutting tool wherein the outer diameter is uniform allowing both precise cutting of a small hole, and allowing easy removal by simply pulling the device out without unthreading, wherein the perforator has an upper end adapted to be connected to a motorized dental hand piece; and, wherein the perforator has a rod therein which turns with the perforator needle-like cutting tool assisting in preventing debris from entering the perforator: and wherein the perforator serves as a catheter for accommodating a hypodermic needle having a same outer diameter as the rod, after the catheter is inserted into the bone.

It is the belief of the inventor, that this novel method and combination of elements will eventually change the way in which many dentists infuse medication and local anesthesia.

Unlike the prior art catheters the catheter drill of the instant invention will not bind or increase its resistance against the drilling hand piece as it is drilling into the bone. The uniform outer diameter allows the drill/needle to cut without binding and acting as a self-tapping hollow screw.

In addition to this novel way of performing dentistry, there is preferred embodiment of this invention which facilitates use of the device in more difficult to access areas of a patient's mouth, for example, when it is required to access molars in the back of the mouth. In order to reach these otherwise difficult to reach areas with medication, after the catheter drill resides in its targeted area, an adapter for injecting fluid al a right angle to the longitudinal axis of the catheter drill is provided.

Furthermore, this adapter can be used or embodiments thereof are provided which obviate the use of a syringe equipped with a hypodermic needle.

Advantageously, this invention provides an adapter for coupling with the interosseous catheter drill that allows fluid to be injected without having to locate the tip of a hypodermic needle into the catheter, which can be difficult.

SUMMARY OF THE INVENTION

The present invention endeavours to mitigate the problems and disadvantages of delivering dental anaesthetic encountered with the prior art methods and devices.

The present invention provides a perforator having a central passage, which perforator then remains in place as a catheter for allowing a hypodermic needle to be inserted through the passage to deliver the desired medication. The preferred apparatus is provided with means for obstructing the entry of debris in the perforator's passage.

In accordance with the invention, there is provided a device for perforating the periodontal ligaments, cortical plate or small bones, and the like and for injecting substances at a predetermined site, comprising:

perforator for drilling a hole into the ligament, bone or tissue, wherein said perforator is provided with an inner passage to form a catheter adapted to remain in the hole for directing a hypodermic needle to the predetermined site; and an adapter for coupling to an end of the perforator and for latching a latching-type powered dental handpiece thereto and for transmitting rotational movement from the powered dental handpeice to said perforator, the perforator having a drilling needle extending from an end thereof, the drilling needle having a uniform outer diameter and a smooth non-varying outer surface allowing removal once inserted into the periodontal ligaments, cortical plate or small bones and the like by withdrawing the needle by pulling backwards along a line defined by a longitudinal axis of the inserted drilling needle; the adapter for coupling with the perforator in a locking engagement such that rotational motion imparted to the adapter, rotates the perforator when the adapter is coupled with the perforator, the adapter having an upper end having a driving shank extending along a rotational axis for removably engaging the powered dental hand tool, the adapter having a rod sized to be accommodated within the perforator and sized to fit into a passage in said drilling needle at a lower end thereof.

In a further aspect, the rotary drive shaft comprises an axial rod adapted to be inserted into the hollow drilling catheter when engaging it.

According to another aspect of the present invention, there is provided a device for perforating the periodontal ligaments, cortical plate of small bones, and the like, for injecting substances at a predetermined site, comprising: a perforator for drilling a hole into the ligament, bone or tissue, wherein said perforator is provided with an inner passage to form a catheter adapted co remain in the hole perforated for directing a hypodermic needle to said predetermined site, and an adaptor for latching in a latching-type powered dental handpiece for transmitting rotational movement to said perforator, the adapter having a rod at an end thereof sized to be disposed within the perforator inner passage.

The catheterized intra-osseous delivery system of the present invention comprises a perforator with a bevelled drilling needle that is used as a drill and a catheter. The needle is attached at one end to a plastic or metal body. For drilling, the body is attached to a matching adaptor provided with a driving shank which is rotated by a conventional contra angle or straight dental hand piece. Then, the perforator is used as a catheter, whereby a hypodermic needle is inserted through the drilling needle without losing access to the already perforated bone.

In the preferred form of the invention the apparatus is disposable. Before disposal, the perforator receives a cap over the needle for protection against accidental contamination of environment.

The present invention also provides a method of medical treatment, comprising the steps of: inserting a catheter, at a point in the gingival sulcus between outer tooth surface and marginal gingiva, or through gingiva and cortical plate, to a predetermined depth; and injecting medication or anaesthesia through said catheter.

Advantageously, the system of the present invention provide users with a more secure and less painful method and device for direct access for injecting medication to a target area into the cortical plate of the bone.

In addition, the system facilitates and adds a level of security previously unavailable for the anaesthetic in that it has a sure and immediate effect.

Another advantage of this system is that it provides benefits to the dentists by facilitating the use of a low cost, disposable device.

Still another advantage of this invention is that the risk of contamination is lower than with the current devices. This is because the device is disposable and because the risk of the dental equipment used with the device of the invention becoming contaminated is low.

BRIEF DESCRIPTION OF THE DRAWINGS

These and other features of the invention will become more apparent from the following description of the preferred embodiments, in which reference is made to the appended drawings, wherein:

FIG. 1 illustrates an exploded view of the device showing the component parts and their inter-relationship;

FIG. 2A illustrates the device assembled for drilling;

FIG. 2B illustrated a longitudinal cross-section through the device illustrated in FIG. 2A, taken along line A—A of FIG. 2A;

FIG. 3 shows a detailed view of the area marked on FIG. 2B;

FIG. 3B shows a detailed view of the rod-needle inserted in the perforator cutting/drilling-needle inserted in a different orientation than in FIG. 3;

FIG. 7A shows the device drilling, in the bone tissue; FIG. 7B shows the perforator inserted into the bone tissue and the adaptor de-coupled; and FIG. 7C shows the perforator inserted into the bone tissue as a catheter and a hypodermic needle set: for delivering an injection;

FIG. 11 is a perspective, exploded view of the parts of an alternative embodiment of the invention wherein the catheter and adapter can be temporarily locked while drilling occurs;

FIG. 12 is a sectional elevation of the same catheter assembly; and,

FIG. 13 is a plane view of an additional, optional component of the assembly.

FIG. 14 is a cross sectional view of an alternative preferred embodiment of a catheter wherein the hollow needle protrudes both ends of the hub;

FIG. 15 is a cross-sectional view of an adapter coupled in locked sealing engagement with the catheter shown in FIG. 14; and, FIG. 16 is an alternative embodiment of the adapter having a syringe at one end.

DETAILED DESCRIPTION OF THE PREFERRED EMBODIMENT

Figure 4:
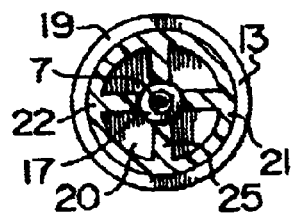
FIG. 4 is a cross-sectional view of the body of the perforator taken along lines B—B of FIG. 2.

FIG. 1 illustrates an exploded view of the device showing the component parts and their inter-relationship. The device comprises a perforator 1, an adaptor 3 and a cap 5.

The perforator 1 has a bevelled drilling needle 7 which is used both as a drill and a catheter. Needle 7 is bevelled at both ends, as better shown on FIG. 2B. The first end 9 is formed as a drilling tip in that it has cutting teeth along the edge, as shown in FIG. 3. The second end 11 is bevelled for receiving and directing the needle of a hypodermic syringe and for easy coupling with the adaptor 3, as will be seen later.

A flange 13 is fixed on the needle about the second end 11, so that the needle passes along the geometrical axis of the flange 13. The flange 13 is manufactured or moulded of a plastic or other material, and it has a generally cylindrical outer shape. This shape is preferred as the flange 13 rotates together with the needle 7 for drilling. Variations of the shape illustrated in the attached drawings may also be contemplated.

The flange 13 is adapted for receiving cap 5 at one end and for coupling with the adaptor 3 at the other end. As an example, a collar 15 may be provided on the flange 13 so that the cap 5 holds over the collar 15 when pressed. The cap 5 is needed to protect and cover the tip 9 of the needle 7 before use and when the device is disposed of.

For ease of manipulation the internal diameter of the cap 5 and the external diameter of the collar 15 should be as large as is reasonable and preferably between 10 to 20 times greater than the diameter of the needle 7. Another advantage of the collar 15 is that it provides a stop to limit the depths of penetration of the needle 7 (the depth of penetration of the needle 7 is, therefore, termed the drilling length, as opposed to the remaining length of the needle 7, which is termed the attachment length). The flange 13 is shaped to form an inner axial shaft 17 projecting from the centre of the collar 15, and a female connector 19 for coupling with a corresponding male connector provided in the adaptor 3.

Figure 5:
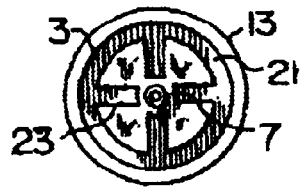
FIG. 5 is a cross-sectional view of the adaptor body.
Figure 6:
FIG. 6 is a cross-sectional view of the cap.

The coupling between the perforator and the adaptor is illustrated on FIGS. 2B, 4 and 5. FIG. 2B shows a longitudinal section of a female connector 19 provided in the flange 13 and a male connector 21 provided in the adaptor 3. FIG. 4 illustrates a cross-section of an exemplary female connector 19, while FIG. 5 shows a cross-section of the corresponding male connector 21. The male connector is provided with radial ribs 23, extending towards the centre but not meeting to leave room for the central shaft 17, while corresponding grooves 25 are provided in the female connector, alternating with islands 20. The female connector is also formed with a clearance ring 22 for accommodating the thickness of the body 29 of the adaptor.

The tubular shaft 17 forms a reinforced passage for drilling needle 7. The shaft also provides enough contact surface between the drilling needle and the body to ensure that these two parts rotate together during drilling. As could be seen on FIG. 2B, end 11 of the needle is bevelled and extends a little over the shaft 17, but there is a clearance between the tip of end 11 and the male connector when the device is assembled for drilling.

When rotated, the drilling needle 7 penetrates in the bone tissue through gingiva or ligament and drills a hole with the cutting tip 9. The perforator 1 may remain in place as a catheter, with the drilling needle inserted into the bone. Then, a hypodermic needle may be introduced through the passage of drilling needle 7 to insect a medicament directly into the bone. Therefore, the drilling needle 7 is selected to have a wide enough passage for allowing a hypodermic needle with a smaller gauge to be inserted through needle 7.

The adaptor 3 has several important functions. Firstly, the adaptor conveys the rotational movement from a dental hand piece or the like to the perforator. As well, the adaptor is provided with means for blocking bone debris for entering into the syringe passage and also aligns and reinforces the needle 7 during drilling. In the preferred embodiment of this invention is it important that the adapter be coupled with the dental hand tool which dives the adapter about its longitudinal axis. It is also important that the adapter conveys its rotational movement from the dental hand piece to the perforator 3. By providing this novel arrangement, after the perforator is inserted into the bone, where it is to remain, all that is required is that the adapter with the dental handpiece be removed from the perforator. Hence the order of dental hand piece driving the adapter including the rod 27 which in turn drives the perforator and its drilling needle is important in the preferred embodiment.

The adaptor includes a rod 27, a body 29 and a shank 31.

Body 29 includes male connector 21 which is formed, as indicated above, with longitudinal ribs 23 which couple with grooves 25 of the female connector 19 for driving needle 7. The shank 31 extends along the axis of the adaptor and is formed with a joint 33 for attachment with a contra-angle or straight hand piece. The shank 31 has a groove 35 and a cut-out 31 to fix the shank in place in the known manner. Generally, the shank transmits to the needle 7 the rotational movement from the hand piece.

The shank 31 also acts as a barrier for contamination, at it is generally thought that bacteria is reluctant to change direction, and there are a plurality of 90° angles between the tip 9 of drilling needle 7 and the joint 33.

The rod 27 has the diameter and length selected in accordance with the size of needle 7. The rod 27 is fixed in the geometrical centre of body 29 so as to readily penetrate into the hollow passage of the needle, when the device is assembled for drilling. When the rod 27 is inserted within the needle passage, it advances through the length of the needle up to the bevelled end, as shown on FIGS. 2A and 3 and 3B in dotted lines. In this way, the debris from drilling cannot penetrate to block the needle passage. In addition, the rod gives additional rigidicy, strength and alignment to needle 7 during drilling. The rod also advances through the a portion of the shank as is illustrated in FIG. 2B in dotted lines. Furthermore, the rod which can itself be in the form of a needle similar to the hypodermic needle for delivery of medication, wherein the rod end is sharp and pointed, to assist in the drilling process. By using standard hypodermic needle tubing for the rod, the cost of the device can be minimized while gaining the benefit of the cutting tip. In manufacture, the cutting tip of the drilling needle 7 and the rod can be cut at the same time to a desired length.

Figure 8:
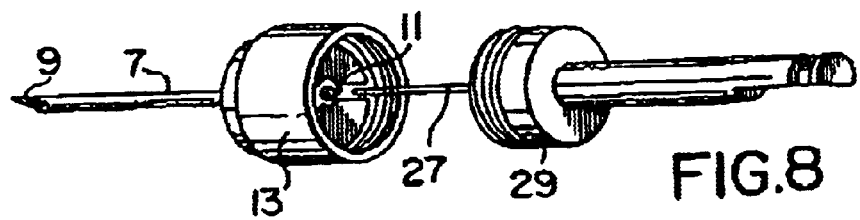
FIG. 8 illustrates another embodiment of the invention.

FIG. 8 illustrates an alternative embodiment of the present invention. In this variant, body 13 is provided with an internal thread while body 29 is provided with a matching external thread. By threading one to the other and using the central rod 27 to align the two bodies together, the perforator could be driven by the hand piece in a similar manner as in the variant disclosed above. Of course, the thread is going in an opposite direction to the direction of rotation of the device for avoiding disconnection of the two bodies.

Figures 9, 10:
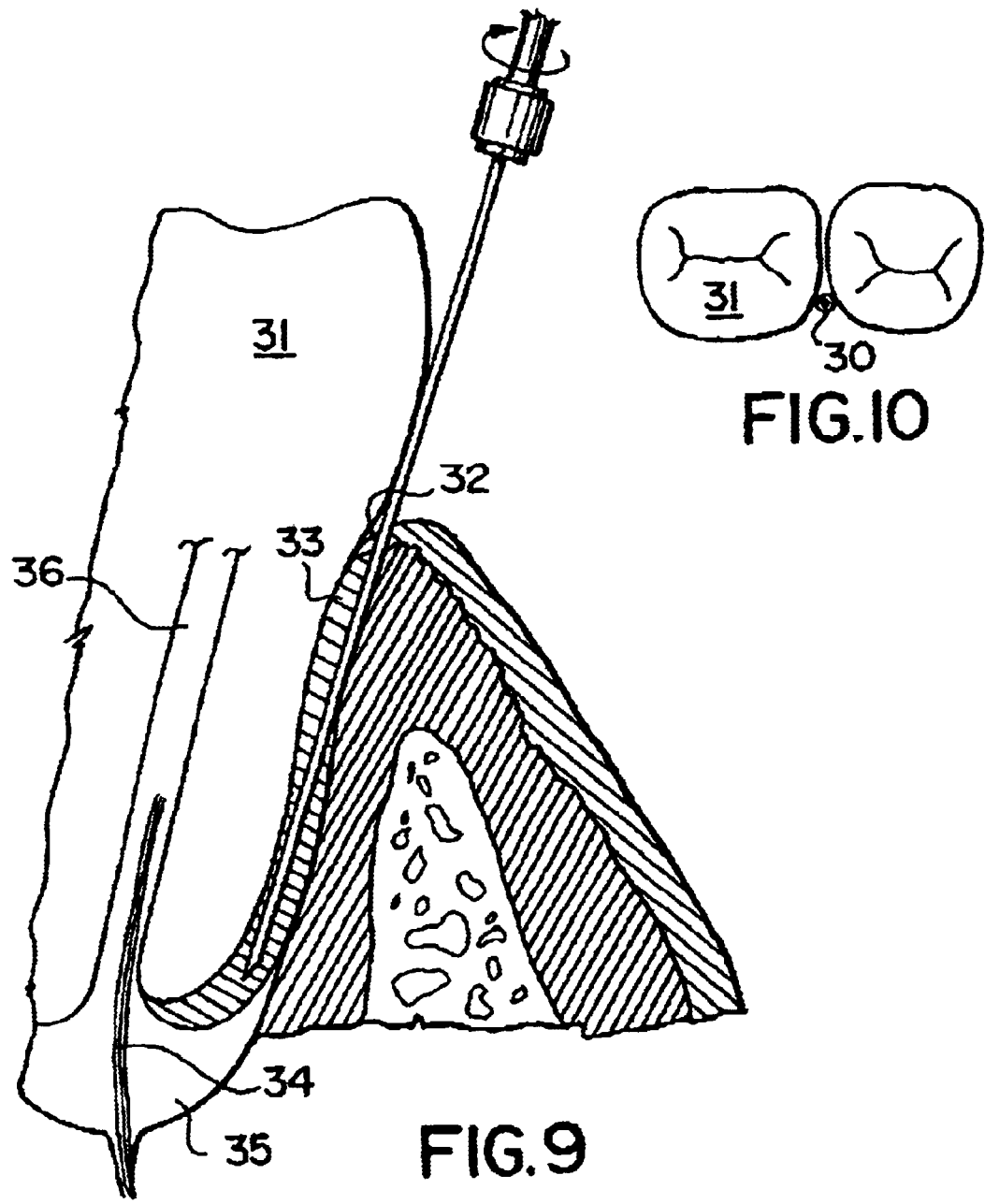
FIG. 9 illustrates an alternative method of delivery medication to treat a root-canal nerve.
FIG. 10 illustrates from a plan view the point of catheter insertion for the alternative method shown in FIG. 9.

An alternative method of targeted delivery is shown in FIGS. 9 and 10. The perforator 7 is inserted at a point 30 between teeth, parallel to the tooth 31 in treatment, and penetrates through gingival sulcus 32 and ligament 33 to a depth near the entry of the nerve, artery and vein bundle 34 through the bone 35 and into the tooth-root canal 36. This method of targeted delivery, say, of anaesthesia is suitable, where perforating vertical to the tooth through gingiva and cortical bone is not convenient or possible; as in the case of rear molars.

There are a variety of ways chat this invention can be devised but the end result is to perform catheterized intraosseous delivery system.

The device of this invention operates as follows:

First, a site for the injection is selected by the practitioner. The gingiva over the injection side is disinfected and topically anaesthetized. A small amount of anaesthetic solution is injected until blanching of the tissue, and this will anaesthetize the gingiva and the periosteum. The following operations are illustrated in FIGS. 7A, 7B and 7C, and FIGS. 9 and 10.

Figure 7A:
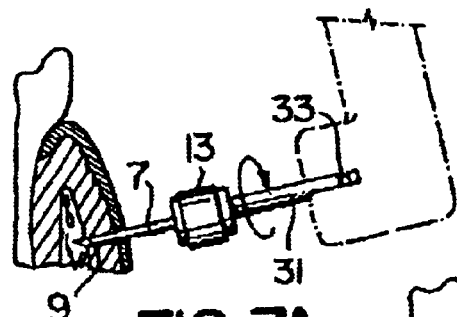
FIGS. 7A–7C illustrate the method according to the invention.

As can be seen in FIG. 7A, the bevelled end 9 of the needle 7 is placed against the gingiva and shank 31 is attached with joint 33 to a contra angle or to a straight dental hand piece. The adaptor and perforator are coupled for drilling.

The perforator should be held perpendicular to the cortical plate, or if not possible or convenient, it should be held vertical and parallel to the long axis of the tooth as shown in FIG. 9, having been inserted between teeth as shown in FIG. 10. The perforator is then operated in small bursts of rotation from the hand piece until resistance is no longer felt, as is well known to dentists.

Figure 7B:
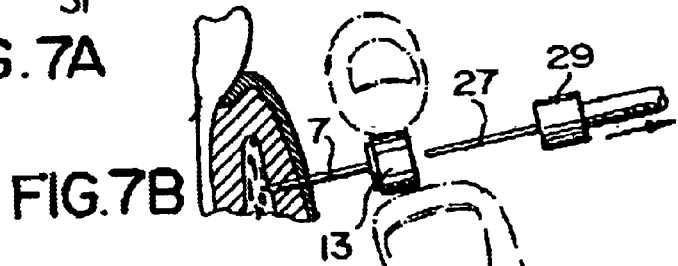

Next, the adaptor 3 is removed from the engagement with perforator 1 by applying pressure to the body 13 with the fingers thus keeping the needle 7 in the perforated cortical plate. This is shown in FIG. 7B.

Figure 7C:
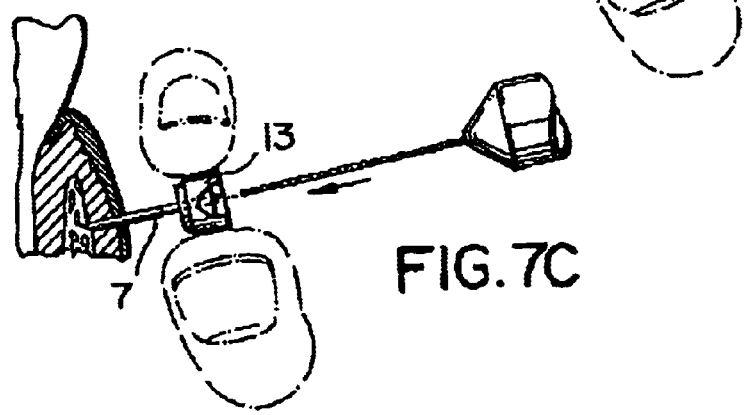

The presence of the needle 7 in the cortical plate, or down the side of the tooth as in FIG. 9, allows an injection to be made without complicated manoeuvres to find the perforation in the case of floating gingiva or the free or marginal gingiva. FIG. 7C illustrates the next step, namely how the injection needle is inserted through the perforator 1 for delivering the anaesthetic solution required.

The last step is to remove the perforator 1 from the cortical plate and reinstall the cover cap 5 over the needle 7, then insert the adaptor to the perforator making the unit complete and disposable. The cap 5 provides a means whereby the apparatus may be removed from the dental hand piece without any risk of the user being in contact with body fluids which will be present on the needle after use. This is extremely important particularly since there may be a risk of contacting Aids or Hepatitis should the user accidentally prick a finger with the needle. It is therefore desirable that the cap should be of a hard or rigid rubber or plastic material not easily penetrated by the needle.

Referring to FIGS. 11 and 12, the catheter assembly comprises a disposable contamination protective cap or housing 10 which, in the assembled state, surrounds a rotatable hollow drill bit or catheter 11, preferably of stainless steel, having a drilling tip 12 and a non-drilling end with an outwardly flaring end portion 13. The end portion is fixed, and preferably molded, within a cylindrical driven flange 14 which is made of plastic material and is disposable along with the rotatable hollow drill bit.

The flange is adapted to be driven by the drive means including a drive flange 16 which has a periphery matching radius of the flange 14, and which is integrally formed with a shaft 17 suitably dimensioned to fit into the handpiece of a standard dental drill; the diameter of this shaft being preferably between 2.27 and 2.45 mm. Parts 16 and 17 may either be metal or plastic, and will also normally be considered disposable. The flange 16 and shaft 17 have an axial bore into which is secured a rod 20 having a cutting tip (not shown) which projects from the flange 17 by an amount equivalent to the main drilling length of the needle 11, and which prevents the needle from becoming blocked with debris during operation.

The driven flange 14 and the drive flange 16 each have a longitudinal groove, indicated respectively at 14a, 16a. When all the parts are assembled, these grooves are occupied by a longitudinal internal rib 21 in the cylindrical wall of the a locking sleeve 22. This is a thin-walled, disposable cap-type part, the cylindrical wall of which is capable of substantially enclosing the two flanges 14 and 16, and having an upper end flange 22a which, when the sleeve is fully engaged with the two flanges 14 and 16, rests against the upper surface of the flange 16. The sleeve 22 serves to hold the flanges together, as well as transmitting rotary motion from the drive to the driven flange. The sleeve is a push fit within the housing 10.

The parts are sold in the assembled condition as shown in FIG. 12. For use the housing 10 is removed, the shaft 17 is fitted into a drilling machine, and a drilling proceeds in the normal way. After drilling, the shaft 17 with flange 16, and rod 20 and sleeve 22, are removed from the flange 14, and anaesthetic is then introduced through the needle 11 which then acts as a catheter.

All parts of the assembly are disposable after use.

FIG. 13 shows a further feature of this embodiment, namely a holder 30 which comprises a rod 30a fixed at one end to part circular clip portion 30b which is formed to encircle a circumferentially grooved central area 14b of the flange 14. This holder may be placed in position to hold the flange 14 after drilling has taken place, with its rod 30a lying along side of the patients mouth and preventing undesirable movement of the flange 14 during the injection step.

In summary, this invention provides particular advantages not suggested in prior art devices. The provision of an adapter piece having a rod at a lower end, a shaft at an upper end for coupling with a motorized dental handpeice, and an intermediate hub disposed between the rod and the shaft wherein the hub has means for locking with a catheter having a drilling needle provides numerous advantages. The drilling needle has a uniform outer diameter and can be withdrawn by simply pulling it out. The adapter is designed to prevent the drilling needle from becoming blocked during drilling and is designed to turn the drilling needle when powered by the handpeice. More importantly, when the catheter has drilled the hole in the bone, the adapter can be removed with the handtool leaving the catheter in place.

Numerous other embodiments can be envisaged without departing from the spirit and scope of the invention. For example, the end of the rod can be provided with a cutting tip assisting the cutting needle in drilling the hole. Furthermore, the rod itself can be a square rod for engaging a complementary recess in the catheter opening. This embodiment would allow the device to function even if the rod was partially extracted during the drilling of the hole as any portion of the square rod could be used to drive the cutting needle.

Although the device described heretofore and shown in the figures is performs satisfactorily, and locating and disposing the drill into the bone at a desired location is relatively simple, it would be advantageous to provide easier access to the catheter once in place about the molars and teeth in general at the back of a patient's mouth. Locating the opening at the top of the hub, i.e. the opening of the drilling needle with the hypodermic needle can be an onerous task. It would be preferred to connect a sleeve or tube to the top of the drilling needle so that a medication supply could be provided thereto.

Turning now to FIGS. 14 and 15, the catheter assembly comprises a hollow drilling needle or catheter 140, having a lower pointed end 141a and an upper pointed end 141b, preferably of stainless steel; the lower end 141a is designed to cut as it rotates and the non-drilling upper pointed end serves to puncture a rubber membrane 152 of an adapter 151. As in previous embodiments, a rod 143 and upper housing 145 are adapted to fit over and within the drilling needle 140. The adapter 151 has lockable clips 154a and 154b for locking into engagement with the recesses 146 within the hub 148. The adapter conveniently serves as an extension that extends the length and the size and angle of the access port of the catheter when in place so that inserting the hypodermic needle 158 containing medication becomes much simpler. Of course the body of the adapter 151 can be rigid. In another embodiment not shown a flexible adapter is provided.

The adapter shown in FIG. 15 is used as an extension passage, for extending the length and orientation of the catheter. However, the adapter shown in FIG. 16 serves as both an extension of the catheter and as a syringe, obviating the requirement to provide a hypodermic needle.

Figure 16:
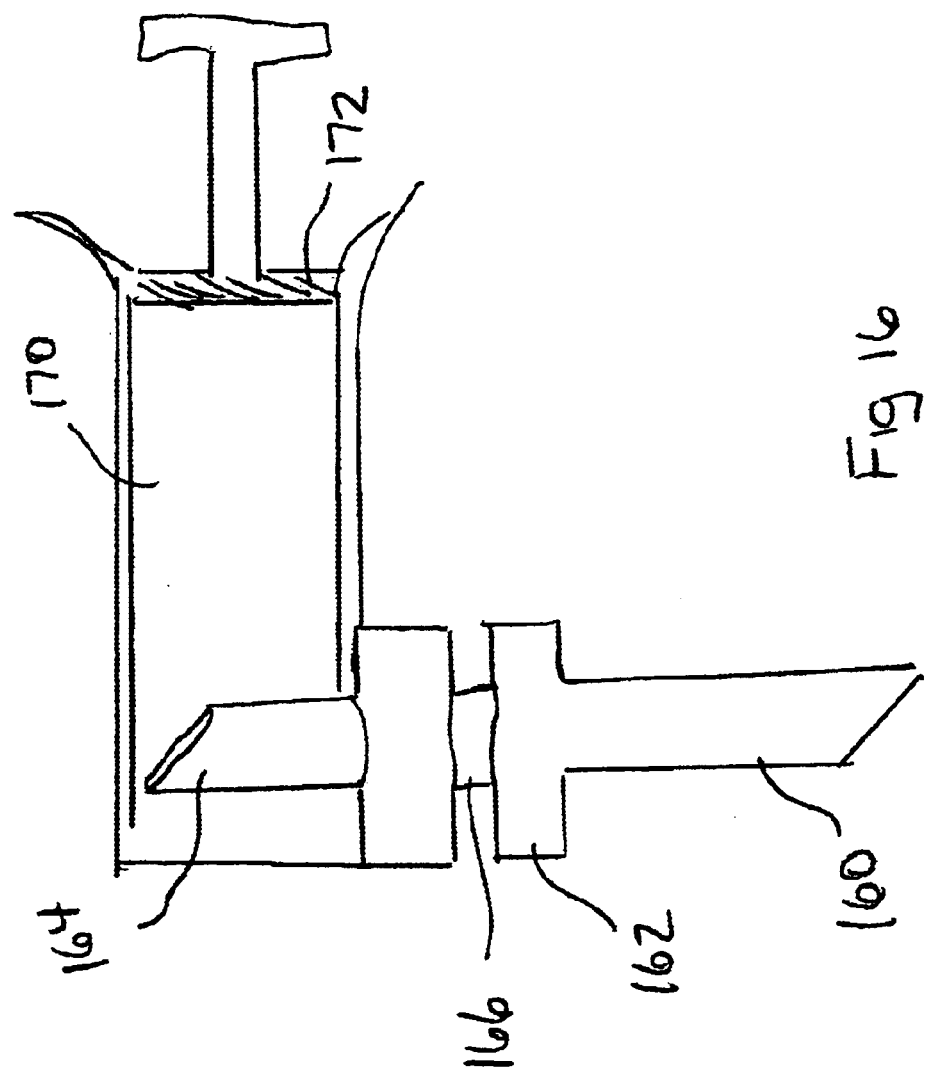

Turning now to FIG. 16 a drilling needle 160 is shown having a hub 162 from which a piercing upper needle 164 extends at an upper end. A clip 166 holds the hub in place as is shown in FIG. 17 which is a front end view of the device shown FIG. 16. A syringe 170 housing medication includes a plunger 172 includes the clip which engages the hub, mating the two together. This is clipped on after the drilling needle has been inserted, and the rod removed.

What is claimed is:

1. A rotatable drilling device for use in injecting medication, said rotatable drilling device comprising:
   a) a rotatable hollow drill bit, wherein the rotatable hollow drill bit includes a first hub and a needle having a first outer diameter extending outwardly from an end of the first hub, the first hub being immovably affixed to the needle so that when the first hub is rotated, the needle is rotated with the first hub, wherein the needle has a sharp tip at an end, wherein the rotatable hollow drill bit has a bore extending therethrough through which medication can be introduced into the bore; and,
   b) an adapter having a rod at a lower end for removable insertion in the bore of the rotatable hollow drill bit, wherein the rod when inserted into the bore extends into and through the needle for substantially preventing debris from entering the needle and blocking the bore when drilling, wherein the adapter has an upper end for directly removably coupling with a motorized handpiece and has a second hub immovably coupled with the rod for directly mating with the first hub of the rotatable hollow drill bit, so as to impart rotational motion to the rotatable hollow drill bit when the upper end of the upper end of the adapter is rotated by the motorized handpiece.

2. A device as defined in claim 1 wherein the rod has an outer diameter that is substantially the same as the inner diameter of the hypodermic needle.

3. A device as defined in claim 2, wherein the rod has a cutting tip and wherein the rod is rotated with the drilling hypodermic needle and wherein the rod and the drilling hypodermic needle drill the hole simultaneously.

4. A device as defined in claim 1 further comprising an adapter for mating with the hub of the rotatable drill bit, the adapter being an L-shaped adapter for use on anterior teeth.

5. A device as defined in claim 1 further comprising an adapter for mating with the hub of the rotatable drill bit, the adapter having a syringe for injecting the substance.

6. A two-piece rotatable drilling device for use in injecting medication or anesthetic, said two-piece rotatable drilling device comprising:
   a) a rotatable catheter hub and a hollow needle having a first outer diameter extending outwardly from an end of the rotatable catheter hub, the rotatable catheter hub being immovably fixed about the outer periphery of the hollow needle, wherein the needle has a sharp tip at an end, wherein the rotatable catheter hub has bore extending therethrough through which medication or anesthetic can be introduced into the bore and into the hollow needle; and,
   b) an adapter piece having a rod at a lower end for removable insertion in the bore of the rotatable catheter hub and hollow needle, wherein the rod when inserted into the bore extends into and through the needle for substantially preventing debris from entering the needle and blocking it when drilling, an upper portion of the adapter adapted to removably couple with a motorized handpiece for rotation therewith when coupled thereto, the adapter piece having a hub for mating with the catheter hub so that rotation of the hub of the adapter rotates the catheter hub when mated therewith.

* * * * *

(12) INTER PARTES REEXAMINATION CERTIFICATE (0214th)
United States Patent
Gibbs

(10) Number: US 6,905,486 C1
(45) Certificate Issued: Nov. 30, 2010

(54) DEVICE FOR TARGETED, CATHETERIZED DELIVERY OF MEDICATIONS

(75) Inventor: David Gibbs, Ottawa (CA)

(73) Assignee: Introsan Dental Products, Inc., Ottawa, Ontario (CA)

Reexamination Request:
No. 95/001,005, Sep. 19, 2007

Reexamination Certificate for:
Patent No.: 6,905,486
Issued: Jun. 14, 2005
Appl. No.: 10/234,767
Filed: Sep. 5, 2002

Related U.S. Application Data

(63) Continuation-in-part of application No. 09/420,004, filed on Oct. 18, 1999, now Pat. No. 6,468,248, which is a continuation of application No. 09/255,442, filed on Feb. 22, 1999, now abandoned, which is a continuation of application No. 09/022,314, filed on Feb. 11, 1998, now abandoned, which is a continuation of application No. 08/471,372, filed on Jun. 6, 1995, now Pat. No. 5,762,639.

(51) Int. Cl.
*A61B 17/88* (2006.01)
*A61B 17/34* (2006.01)

(52) U.S. Cl. .......................... 604/264; 604/272; 433/80; 433/165; 606/80

(58) Field of Classification Search ........................ None
See application file for complete search history.

(56) References Cited

U.S. PATENT DOCUMENTS

| | | | | |
|---|---|---|---|---|
| 1,539,637 A | * | 5/1925 | Bronner | 433/81 |
| 4,258,722 A | * | 3/1981 | Sessions et al. | 600/566 |
| 5,372,583 A | * | 12/1994 | Roberts et al. | 604/506 |
| 5,779,708 A | * | 7/1998 | Wu | 606/80 |
| 6,247,928 B1 | * | 6/2001 | Meller et al. | 433/80 |

* cited by examiner

*Primary Examiner*—Catherine S. Williams

(57) ABSTRACT

Apparatus and method for catheterized delivery or infusion of medication and anaesthesia are disclosed. The perforating catheter is first used to perforate the periodontal ligament and/or the cortical plate of bone tissue, and is then left in place and used as a catheter for insertion of a hypodermic needle of smaller gauge to deliver medication or anaesthesia to a target area. The perforator is a bevelled needle for drilling into the ligament or bone tissue. For drilling, the device comprises an adaptor which transmits the rotational movement from a dental hand piece or the like to the bevelled needle. A cap is also included for protecting the bevelled needle during storage of the device. The adaptor may have a rod which extends axially into the bevelled needle when the device is assembled for drilling. The rod is used to prevent the debris resulting from drilling from blocking the passage in the bevelled needle. As well, the rod reinforces the needle and maintains the alignment between the perforator and the adaptor for improved drilling efficiency. An adapter is disclosed which couples with the catheter once in place easing access to supply medication to difficult to reach areas.

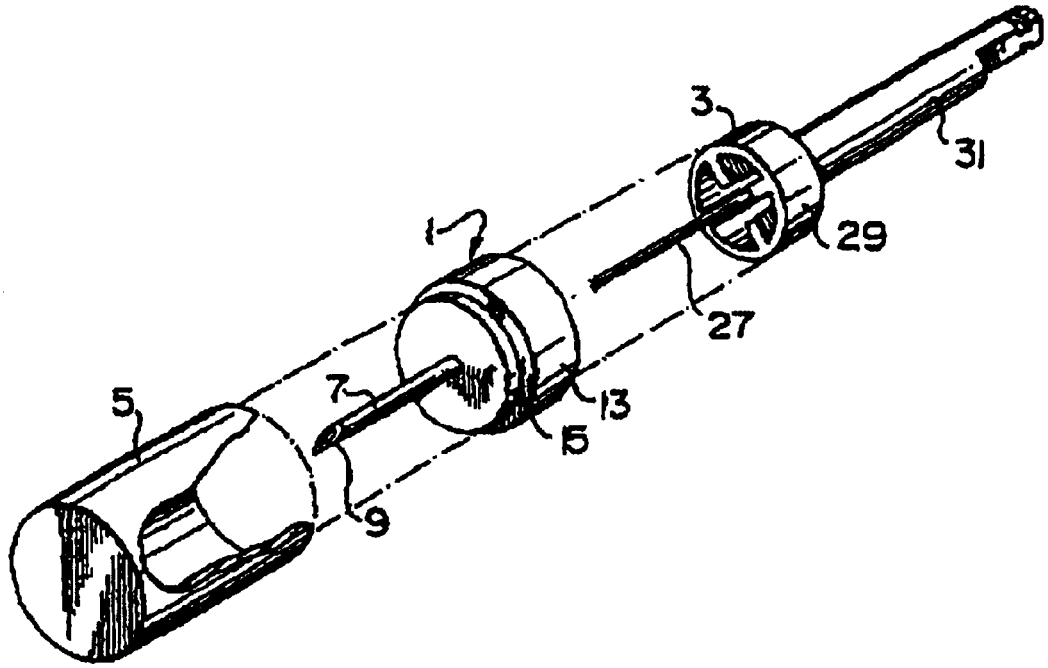

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-6 are cancelled.

\* \* \* \* \*